United States Patent [19]
Peng et al.

[11] Patent Number: 5,858,735
[45] Date of Patent: Jan. 12, 1999

[54] PROCESS FOR PRODUCING TREHALOSE

[75] Inventors: Jin-Torng Peng, Ta-Li; Shou-Hsiung Pai, Taipei; Ae-Ning Lin, Taipei; Mei-Wen Chen, Taipei, all of Taiwan

[73] Assignee: Development Center for Biotechnology, Taipei, Taiwan

[21] Appl. No.: 951,711

[22] Filed: Oct. 16, 1997

[51] Int. Cl.$^6$ ............ C12P 19/12; C12P 19/00; C07H 3/02
[52] U.S. Cl. .......... 435/100; 435/72; 536/123.13
[58] Field of Search ............ 435/100, 72; 536/123.13

[56] References Cited

FOREIGN PATENT DOCUMENTS

| 0 555 540 A1 | 8/1993 | European Pat. Off. ........ C12P 19/12 |
| 0 628 630 A2 | 12/1994 | European Pat. Off. ........ C12N 9/24 |
| 9-140285 | 11/1995 | Japan . |

OTHER PUBLICATIONS

Hammond, Phytochemistry 19:2565–2568 (1980).
Chemical Abstracts 107(11):93646f (1987).
Chemical Abstracts 109(9);71939t (1988).
Chemical Abstracts 111(13):112320w (1989).
Chemical Abstracts 125 (17):216569q (1996).
"Production of Trehalose by Enzymatic Conversion from Starch", Bio Science & Industry, vol. 53:777–779, 1995.
Hull et al., "Trehalose as a Common Industrial Fermentation Byproduct", Carbohydrate Research 266:147–152 1995.
Kidd et al., "Trehalose is a Sweet Target foir Agbiotech", Bio/Technology 12:1328–1329, 1994.
Maruta et al., "Cloning and Sequencing of Trehalose Biosynthesis Genes from Arthrobacter sp. Q36", Biochimica et Biophysica Acts 1289:10–13, 1996.
Maruta et al., "Formation of Trehalose from Maltooligosaccharides by a Novel Enzymatic System", Biosci. Biotech. Biochem. 59:1829–1834, 1995.
Miyazaki et al., "Trehalose Accumulation by a Basidiomycotinous Yeast, Filobasidium Floriforme", J. cf Fermentation and Bioengineering 81:315–319, 1996.

*Primary Examiner*—Francisco Prats
*Attorney, Agent, or Firm*—Fish & Richardson P.C.

[57] ABSTRACT

A process for obtaining trehalose by growing a fungus of the genus Pleurotus in a liquid or solid medium and purifying the trehalose produced by the fungus.

7 Claims, No Drawings

PROCESS FOR PRODUCING TREHALOSE

BACKGROUND OF THE INVENTION

Trehalose is a disaccharide consisting of two glucose units and has a sweet taste.

Trehalose has been used as a preservative, a stabilizer, a cell activity-retaining agent, a moisture-retaining agent, a cold-resistant agent, and an anti-freezing agent in industries as diverse as foods, cosmetics, and pharmaceuticals. Also, as a non-reducing sugar, trehalose does not react with amino groups and therefore does not cause undesirable browning and deterioration of organic substances. Thus, it is an attractive sweetener for certain foods.

Several methods of producing trehalose have been established, including those based on extraction, fermentation, culturing, and enzymatic conversion. For example, two enzymes, maltooligosyl trehalose synthase and maltooligosyl trehalose trehalohydrolase, have been used to convert maltooligosaccharides to trehalose (Maruta et al., Biosci Biotech Biochem 59:1829–1834 [1995]). As another example, the genus Brevibacterium has been used to produce trehalose in a fermentation process (Tsuchida et al., European Patent No. 0555540A1 [1993]).

SUMMARY OF THE INVENTION

The present invention provides a process for obtaining trehalose. The inventors of the this process have found that members of the fungus genus Pleurotus have the ability to produce a large amount of trehalose.

The process of the invention includes two steps: (1) growing a Pleurotus species in a medium and (2) purifying the trehalose produced from the fungus. By "purifying trehalose" is meant enriching trehalose to a commercially acceptable degree.

When *P. eryngii* is used, it is preferred that the trehalose be isolated from the fungus grown to a specific stage in its life cycle (i.e., stage 4, described in Example 1 below).

The medium of the above process may be a solid or liquid medium. A "solid medium" is defined as a substrate containing at least one kind of lignocellulose as the main component which can be supplemented with organic nutrients with a better yield of the fungus. A "liquid medium" is defined as a solution or suspension containing any nutritious substances which can support the mycelial growth or fructification of the fungus.

Other features or advantages of the present invention will be apparent from the following detailed description and from the claims.

DETAILED DESCRIPTION OF THE INVENTION

A fungus belonging to the genus Pleurotus is grown in a medium, and the trehalose produced by the fungus is purified. All fungi, wild-type or mutants, of the genus Pleurotus having the ability to produce trehalose, i.e., the fungi having the enzymes which can convert maltooligo-saccharides or polysaccharides to trehalose, are suitable for practicing the method of the present invention. Examples of fungi from the Pleurotus genus, which can be used as a source of trehalose include: *P. ostreatus* (ATCC No. 52947), *P. eryngii* (ATCC No. 36047), *P. citrinopileatu* (ATCC No. 60892), *P. cystidiosus* (ATCC No. 48751 or 48752), *P. pulmonarius* (ATCC No. 42049), *P. sajor-caju* (ATCC No. 32078), *P. elongatipes* (ATCC No. 52944), and *P. passeckerianus* (ATCC No. 9416).

The solid medium used to practice the method of this present invention contains at least one source of lignocellulose and, if sawdust is used as the source of lignocellulose, additionally contains at least one source of organic nutrients. Possible sources of lignocellulose include sawdust, straw (such as rice straw), and cottonseed hulls. Sources of organic nutrients include rice bran, cornmeal, yeast powder, soybean meal, and wheat bran. The medium may be solid or liquid, and a buffering agent, e.g., calcium carbonate, may be added to the medium to adjust the pH.

The Pleurotus fungus may grow to form mushrooms. The mushrooms, having a high content of trehalose, and can be collected as a source of trehalose. The trehalose can be extracted from the mushrooms with a solvent which is capable of dissolving trehalose (e.g., water). To increase the extraction efficiency, the solvent may be heated prior to extraction. Trehalose may also be obtained from the medium.

Purification of trehalose can be achieved using, for example, ion exchange chromatography or ethanol crystallization.

Without further elaboration, it is believed that one skilled in the art can, based on the above disclosure and the purification of trehalose from the three Pleurotus species described below, utilize the present invention to its fullest extent. The following examples are to be construed as merely illustrative of how one skilled in the art can obtain trehalose from any species of the genus Pleurotus, and are not limitative of the remainder of the disclosure in any way whatsoever. Any publications cited in this disclosure are hereby incorporated by reference.

EXAMPLE 1

Sawdust of broad-leaved trees and rice bran were mixed with water, and calcium carbonate was added to the mixture to achieve a pH of 6.5. More water was added to a final water content of about 65%. The above substrate ingredients were mixed thoroughly and used to fill polypropylene bottles using an automatic or semi-automatic filling machine. The bottles were then pierced, and a lid was put on each of them.

The substrate-filled bottles were sterilized, cooled, inoculated with *Pleurotus eryngii* spawn, and incubated at 18°–22° C. with 80% humidity. When the mycelia were grown throughout the substrate in a bottle, the lid was taken off. The spawn remained on the bottle neck, and the mycelia layer (about 1 cm deep) on the surface of the bottle neck was removed. Subsequently, the lid was put on the bottle again, and the bottle was moved into a cropping room maintained at 16.5°–18.5° C. with 95% humidity to stimulate the formation of mushrooms.

When most of the mycelia layer on the bottle neck formed into water droplets or pinheads, the lid was removed and the humidity was lowered to about 90% to avoid the formation of too many pinheads because of the undesirable high water content of such structures. When the bottle was first moved into the cropping room, no light was needed. However, when water droplets or pinheads were formed on the bottle neck, weak light (about 125–250 lux) should be given to help the development of pinheads into normal fruiting bodies.

Alternatively, the substrate ingredients were placed in polypropylene bags instead of bottles. Each of the bags was pierced, and the opening portion of the bag was closed by a plastic ring and sealed with cotton. When the mycelia were grown throughout the substrate, the cotton and ring were removed. Subsequently, the bag was moved into a cropping room to stimulate the formation of fruiting bodies. other procedures which were not specified were the same as for the bottles.

Mushrooms were harvested at different growth stages, which are defined as follows:

Stage 0: Mycelia accumulated together to form a tissue block; no pinheads formed.

Stage 1: Pinheads differentiated into pilei and stipes; gills not yet differentiated into pilei; 1–1.5 cm fruiting body height.

Stage 2: Pilei differentiated into gills; pilei and stipes distinguishable; 1.5–3.0 cm fruiting body height.

Stage 3: Basidiospores not yet formed in gills; 3–5 cm fruiting body height.

Stage 4: Basidiospores formed in gills but edges of gills not yet curled upwards; 5 to 8 cm fruiting body height.

Stage 5: Some basidiospores fallen from gills; gills curled upwards slightly; 8–12 cm fruiting body height.

The mushrooms at different growth stages were picked and the stipes and pilei separated. The mushroom parts were immediately dried in an oven at 105° C. for 20 hours. About 5 to 10 g of the dried mushrooms were cut into short sections (i.e., about 0.5 cm long) and then extracted by pure water (of a weight of about 17 times that of the mushrooms) and refluxed in a 75° C. hot water bath for 1 hour. The resulting mixture was filtered through 0.45 μm filter paper. The filtrate was then recovered and stored at −20° C. for further analysis.

The extract of from stipes was applied to a cation exchange resin SK1B column and an anion exchange resin WA30 column, then filtered through an Amicon YM3 membrane by ultrafiltration/diafiltration. The filtrate was treated with activated carbon in a 60° C. hot water bath for 2 hours and then filtered through a No. 3 filter paper. The filtrate was concentrated to less than 5 ml. The recovery yield of trehalose was about 85%.

Trehalose was measured by high-performance liquid chromatography ("HPLC") using a Beckmann System Gold HPLC, a detector (Waters 410 differential refractometer) with a sensitivity of $5 \times 10^{-5}$, a column (Bakerbond Aminopropyl [$NH_2$] 5 μm, 4.6×25 cm), a column temperature of 30° C., a buffer of 25% $H_2O$ and 75% $CH_3CN$, and a flow rate of 1 ml/min. 0.05 g to 1 g of standard trehalose was diluted with 100 ml of pure water and analyzed by HPLC to obtain a calibration curve. The injection volume was 20 μl.

The filtrates of the stipe and pileus portions of *P. eryngii* mushrooms at different growth stages were harvested and measured by HPLC according to the above method and conditions.

Table 1 summarizes the fresh and dry trehalose yields of the stipe and pileus portions of the mushrooms at different growth stages. The data show that for each growth stage, the amount of trehalose from the stipe was greater than that from the pileus, and the stipe from the stage 4 mushroom had the largest amount of trehalose with a dry yield of 25.8%. Yield is defined as the weight of total trehalose isolated divided by the fresh or dry weight of the mushroom stipes or pilei. Fresh weight refers to the weight of the mushroom, or parts thereof, as harvested. Dry weight

TABLE 1

| Pleurotus eryngii Mushrooms | Fresh weight (g) | Dry weight (g) | Dry/Wet (%) | Volume (ml) | Trehalose Conc. (%) | Trehalose Conc. (mg/ml) | Total Trehalose (mg) | Yield (fresh) (g/g) | Yield (dry) (g/g) |
|---|---|---|---|---|---|---|---|---|---|
| stage 0 | 15.89 | 2.55 | 16.05 | 30.0 | 1.09 | 10.90 | 327.00 | 2.1 | 12.8 |
| stage 1 | 15.26 | 2.01 | 13.17 | 25.5 | 1.28 | 12.80 | 326.40 | 2.1 | 16.2 |
| stage 2 (stipe) | 74.97 | 10.01 | 13.35 | 134.0 | 1.58 | 15.80 | 2117.20 | 2.8 | 21.2 |
| stage 2 (pileus) | 14.10 | 1.90 | 13.48 | 25.8 | 1.03 | 10.30 | 265.74 | 1.9 | 14.0 |
| stage 3 (stipe) | 67.54 | 9.74 | 14.42 | 127.5 | 1.58 | 15.80 | 2014.50 | 3.0 | 20.7 |
| stage 3 (pileus) | 22.40 | 2.75 | 12.28 | 28.0 | 1.16 | 11.60 | 324.80 | 1.5 | 11.8 |
| stage 4 (stipe) | 32.94 | 4.41 | 13.39 | 55.0 | 2.07 | 20.70 | 1138.50 | 3.5 | 25.8 |
| stage 4 (pileus) | 15.18 | 1.66 | 10.94 | 27.7 | 1.23 | 12.30 | 340.71 | 2.2 | 20.5 |
| stage 5 (stipe) | 24.85 | 3.75 | 15.09 | 45.5 | 1.95 | 19.50 | 887.25 | 3.6 | 23.7 |
| stage 5 (pileus) | 19.53 | 2.17 | 11.11 | 24.5 | 1.49 | 14.90 | 365.05 | 1.9 | 16.8 |
| stage 6 (stipe) | 24.79 | 4.10 | 16.54 | 49.0 | 1.82 | 18.20 | 891.80 | 3.6 | 21.8 |
| stage 6 (pileus) | 18.13 | 2.17 | 11.97 | 25.5 | 1.60 | 16.00 | 408.00 | 2.3 | 18.8 | refers to the weight of the fungus after drying in an oven at 105° C. for 20 hours.

EXAMPLE 2

*P. cystidiosus* (purchased from a commercial supplier) was extracted and analyzed according to the process described in Example 1 above. The trehalose dry yield for stage 5 mushrooms (See Example 1 above, except fruiting body height was different) was 10.7%. This yield represented the average of the dry yields for stipes and pilei. In light of this yield, the high yield of trehalose from *P. eryngii*, i.e., an average dry yield of 20.25% at stage 5, was unexpected.

EXAMPLE 3

*P. sajor-caju* (purchased from a commercial supplier) was extracted and analyzed according to the process described in Example 1 above. The trehalose dry yield for stage 5 mushrooms (See Example 1 above, except fruiting body height was different) was 3.3%. This yield represented the average of the dry yields for stipes and pilei. In light of this yield, the high yield of trehalose from *P. cystidiosus*, i.e., an average dry yield of 10.7% at stage 5, was unexpected.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of this invention. For example, use of liquid or solid media other than that described in Example 1 are also comtemplated within the scope of the claims.

What is claimed is:

1. A process for obtaining trehalose, comprising growing a fungus of the species *Pleurotus eryngii* in a medium, and purifying the trehalose produced by the fungus.

2. The process of claim 1, wherein the medium is a liquid medium.

3. The process of claim 1, wherein the medium is a solid medium.

4. The process of claim 3, wherein the trehalose is purified from a pileus of the fungus.

5. The process of claim 3, wherein the trehalose is purified from a stipe of the fungus.

6. The process of claim 3, wherein the trehalose is purified from the fungus grown to stage 4.

7. The process of claim 6, wherein the trehalose is purified from a stipe of the fungus.

\* \* \* \* \*